United States Patent [19]

Morrow

[11] 4,147,805

[45] Apr. 3, 1979

[54] ALKYLTHIOPHENOXYALKYLAMINES AND THE PHARMACEUTICAL USE THEREOF

[75] Inventor: Duane F. Morrow, Evansville, Ind.

[73] Assignee: Mead Johnson & Company, Evansville, Ind.

[21] Appl. No.: 928,668

[22] Filed: Jul. 28, 1978

[51] Int. Cl.$^2$ .................... A61K 31/135; C07C 93/06
[52] U.S. Cl. .................................. 424/330; 260/570.7
[58] Field of Search ...................... 424/330; 360/570.7

[56] References Cited
U.S. PATENT DOCUMENTS

| 3,746,768 | 7/1973 | Bordenca et al. | 260/570.7 |
| 3,808,257 | 4/1974 | Richtner et al. | 424/330 |
| 3,873,620 | 3/1975 | Pinhas | 260/570.7 |
| 3,930,016 | 12/1975 | Berntsson et al. | 424/330 |

OTHER PUBLICATIONS

Med. Chem. 2nd ed., p. 600—Interscience, N.Y.—A. Burger.

Primary Examiner—Albert T. Meyers
Assistant Examiner—D. W. Robinson
Attorney, Agent, or Firm—Robert H. Uloth; Robert E. Carnahan

[57] ABSTRACT

A new class of alkylthiophenoxyalkylamine derivatives and methods for preparation are described. The compounds have vasodilating and antispasmodic activity, inhibit blood platelet aggregation and are substantially free of beta-adrenergic blocking effects. They are particularly valuable in the treatment of disease states responsive to vasodilation such as obstructive peripheral vascular diseases and cerebral vascular deficiencies. Representative and preferred embodiments of the invention are N-[3-[4-(methylthio)phenoxy]propyl]octylamine and N-[3-[4-(1-methylethyl)thio]phenoxy]-propyl]octylamine.

21 Claims, No Drawings

ALKYLTHIOPHENOXYALKYLAMINES AND THE PHARMACEUTICAL USE THEREOF

FIELD OF THE INVENTION

This invention pertains to carbon compounds having drug and bio-affecting properties. It is particularly concerned with new and useful alkylthiophenoxyalkylamines, use thereof in pharmaceutical preparations and therapeutic methods, and process for producing the alkylthiophenoxyalkylamines. The alkylthiophenoxyalkylamines of this invention increase peripheral blood flow, relax vascular smooth muscle, and inhibit platelet aggregation and are considered to be particularly useful in the treatment of obstructive peripheral vascular disease such as intermittent claudication and cerebrovascular deficiencies associated with arteriosclerosis.

As used herein, the term "lower alkyl" refers to a carbon chain comprised of both straight and branched chain carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

As used herein, the term "alkyl" refers to straight or branched chain carbon radicals with the number of carbon atoms comprising the particular alkyl radical specifically designated or referred to by standard notations such as ($C_1$–$C_4$), ($C_1$–$C_8$) and ($C_6$–$C_{12}$).

As used herein, the term "non-toxic pharmaceutically acceptable acid addition salts" refers to salts of compounds of formula I formed with a variety of inorganic and organic acids, the anions of which are relatively non-toxic. Such acid addition salts are considered pharmacologically equivalent to the bases characterized by structural formula I. Examples of useful salt forming acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzenesulfonic, p-toluenesulfonic, and related acids. Acid addition salts of this invention are prepared and isolated by conventional means; for instance, by treating a solution or suspension of the free base in a reaction inert solvent with the desired acid and recovering the salts which form by concentration under reduced pressure or by crystallization techniques or other standard chemical manipulations. Acid addition salts which are somewhat toxic and therefore do not meet the foregoing criteria for pharmaceutical acceptability are sometimes useful as intermediates for isolation and purification of the bases of formula I or for other chemical purposes such as separation of optical isomers. Such salts are also considered part of the invention.

DESCRIPTION OF THE PRIOR ART

Variously substituted phenoxyalkylamines with a broad spectrum of biological activity are known. For example, A. Burger, *Medicinal Chemistry*, 2nd Edition (Interscience, New York), page 600 lists the following beta-phenoxyethylamines.

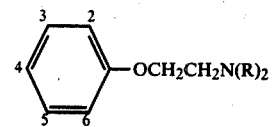

| Nuclear Substituent | R | Activity |
| --- | --- | --- |
| None | piperidine | antipyretic |
| 3-OH | methyl | pressor |
| None | ethyl | sympatholytic |
| 4-$NH_2$ | methyl | nicotinic |
| 2-isopropyl-5-methyl | ethyl | antihistaminic |
| 2-allyl-6-$OCH_3$ | ethyl | oxytocic |
| 2-phenyl | ethyl | antifibrillant |

Pinhas, U.S. Pat. No. 3,873,620 patented Mar. 25, 1975 discloses phenoxyalkylamines of the formula

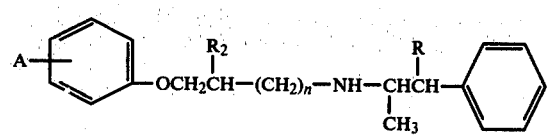

in which n is zero or 1, R is hydrogen or hydroxy, $R_2$ is hydrogen, hydroxy ($R_2$ being other than hydroxy when m is zero) or alkyl and A is $CH_2OH$, $COR^1$, or $CH(OH)R^1$ in which $R^1$ is cyclohexyl or phenyl. The compounds are said to be useful as coronary vasodilators and antispasmodics.

No examples of prior art phenoxyethylamines or phenoxypropylamines having a nuclear alkylthio substituent in combination with an alkylamino moiety are known to applicant.

SUMMARY OF THE INVENTION

Broadly described, the present invention is directed to novel alkylthiophenoxyalkylamines of the formula

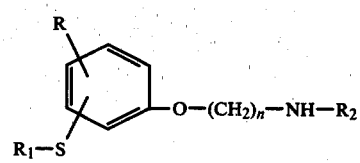

wherein R is hydrogen or lower alkyl of 1 to 4 carbon atoms inclusive; $R_1$ is alkyl of 1 to 8 carbon atoms inclusive; $R_2$ is alkyl of 6 to 12 carbon atoms inclusive; n is the integer 2 or 3; and the pharmaceutically acceptable acid addition salts thereof.

This invention is also concerned with pharmaceutical compositions containing the alkylthiophenoxyalkylamines and further contemplates methods for both producing as well as employing the compounds and compositions therapeutically for the treatment of peripheral vascular disease, other degenerative conditions of the vascular system such as atherosclerosis and other thrombogenic conditions.

DETAILED DESCRIPTION OF THE INVENTION

The alkylthiophenoxyalkylamines provided by this invention are represented by formula I

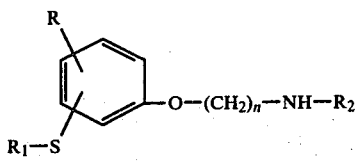

(I)

wherein
R is hydrogen or lower alkyl of 1 to 4 carbon atoms inclusive;
$R_1$ is alkyl of 1 to 8 carbon atoms inclusive;
$R_2$ is alkyl of 6 to 12 carbon atoms inclusive;
n is the integer 2 or 3;
and the pharmaceutically acceptable acid addition salts thereof.

Contemplated subclasses within the ambit of formula I which further characterize the alkylthiophenoxyalkylamines of the invention are compounds of Formula I wherein (Ia) R is hydrogen, $R_1$ is ($C_1$–$C_8$) alkyl, $R_2$ is ($C_6$–$C_{12}$) alkyl, and n is 2 or 3;
(Ib) R is hydrogen, $R_1$ is ($C_1$–$C_8$) alkyl, $R_2$ is ($C_6$–$C_{12}$) alkyl, and n is 3;
(Ic) R is hydrogen, $R_1$ is lower ($C_1$–$C_4$) alkyl with the $R_1S$ radical in the para position, $R_2$ is ($C_6$–$C_{12}$) alkyl, and n is 2 or 3;
(Id) R is hydrogen, $R_1$ is lower ($C_1$–$C_4$) alkyl with the $R_1S$ radical in the para position, and $R_2$ is ($C_6$–$C_{12}$) alkyl, and n is 3;
(Ie) R is hydrogen, $R_1$ is lower ($C_1$–$C_4$) alkyl with the $R_1S$ radical in the para position, $R_2$ is n-octyl, and n is 2 or 3;
(If) R is hydrogen, $R_1$ is lower ($C_1$–$C_4$) alkyl with the $R_1S$ radical in the para position, $R_2$ is n-octyl, and n is 3;
(Ig) R is hydrogen, $R_1$ is isopropyl, $R_2$ is ($C_6$–$C_{12}$) alkyl and n is 2;
(Ih) R is hydrogen, $R_1$ is isopropyl, $R_2$ is ($C_6$–$C_{12}$) alkyl and n is 3;
(Ii) R is hydrogen, $R_1$ is isopropyl with the $R_1S$ radical in the para position, $R_2$ is ($C_6$–$C_{12}$) alkyl and n is 3;
(Ij) R is hydrogen, $R_1$ is isopropyl with the $R_1S$ radical in the para position, $R_2$ is n-octyl, and n is 2 or 3;
(Ik) R is methyl, $R_1$ is lower ($C_1$–$C_4$) alkyl with the $R_1S$ radical in the para position, $R_2$ is n-octyl, and n is 3.

According to one aspect of the instant invention, there is provided a process for preparing an alkylthiophenoxyalkylamine characterized by formula I which comprises reacting an alkali metal salt of an alkylthiophenol derivative of formula II

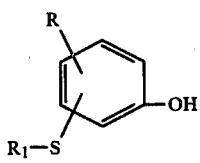

(II)

wherein R and $R_1$ have meanings hereinabove described with 1-bromo-2-chloroethane or 1-bromo-3-chloropropane affording a phenoxyalkyl chloride intermediate of formula III

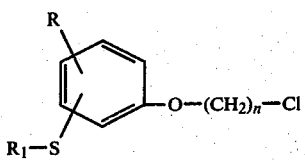

(III)

wherein R, $R_1$ and n have meanings hereinabove described, and condensing the formula III intermediate with an amine of formula IV $$H_2N-R_2 \qquad (IV)$$

wherein $R_2$ has the meaning hereinabove described; whereafter, if desired, the formula I product in free base form is reacted with an acid to form an acid addition salt thereof.

In carrying out the foregoing process, formula II alkylthiophenol alkali metal salts are prepared in conventional manner. For instance, the alkylthiophenol is treated with a suitable alkali metal base such as sodium hydroxide or potassium hydroxide in a reaction inert solvent such as isopropanol, ethanol, and the like. Other standard methods for preparing phenolic alkali metal salts may be employed such as treating the formula II phenol with alkali metal hydrides, e.g., sodium or potassium hydride, in an inert reaction solvent such as 1,2-dimethoxyethane or with an alkali metal alkoxide such as sodium methoxide in a lower alkanol solvent such as methanol, isopropanol and the like.

Condensation of the formula II alkylthiophenol alkali metal salt with 1-bromo-2-chloroethane or 1-bromo-3-chloropropane to provide alkylthiophenoxyalkyl chlorides of formula III is carried out at moderately high temperatures, e.g., between about 50° C. and the reflux temperature of the reaction medium, generally for periods of from 10 to 72 hours.

Condensation of formula III alkylthiophenoxyalkyl chlorides with $R_2$—$NH_2$ amines of formula IV is preferably carried out in the presence of an organic solvent inert under the reaction conditions. Elevated temperature, e.g., reflux temperature of the solvent, are employed to complete the reaction. Suitable solvents include acetonitrile and lower alkanols such as methanol, ethanol, propanol, isopropanol, and the like. Excess amine or an alkali metal carbonate such as sodium or potassium carbonate may be employed to take up HCl formed during the reaction. In the absence of a suitable acid acceptor, a catalytic amount of potassium iodide is preferably employed. The condensation can also be effected in the absence of a reaction solvent by employing a sufficient amount of the amine reactant to serve as the reaction medium.

The required formula II alkylthiophenols are obtained by coupling a diazotized aminophenol with an alkyl mercaptan to form a diazosulfide which is then decomposed providing the corresponding alkylthiophenol. This is a conventional method and adaptations thereof are described in R. B. Wagner, and H. D. Zook, *Synthetic Organic Chemistry*, page 789 (1953 Wiley); E. Miller, et al., J. Am. Chem. Soc., 55, 1224 (1933); S. Asaka, et al., Chem. Abst. 61, 13243a.

Suitable Alkylthiophenol reactants of formula II which may be employed in the present process include:
4-methylthiophenol,
4-ethylthiophenol,
4-n-propylthiophenol, 4-n-butylthiophenol,
4-n-pentylthiophenol,
4-n-hexylthiophenol,
4-n-heptylthiophenol,
4-n-octylthiophenol,
4-isopropylthiophenol,
4-(3-methylbutylthio)phenol,
2-n-butylthiophenol,
3-n-butylthiophenol,
2-ethylthiophenol,
2-n-propylthiophenol,
2-isopropylthiophenol,
3-ethylthiophenol,
3-n-propylthiophenyl,
3-isopropylthiophenol,
2-methyl-4-(methylthio)phenol,
3-methyl-4-(methylthio)phenol.

Suitable amines of formula IV which may be employed in the present process include:
n-hexylamine,
n-heptylamine,
n-octylamine,
n-nonylamine,
n-decylamine,
n-undecylamine,
n-dodecylamine,
n-isooctylamine,
2,2-dimethylhexylamine,
1,1-dimethylheptylamine.

As stated hereinabove, the alkylthiophenoxyalkylamines of the present invention increase peripheral blood flow, relax vascular smooth muscle, and inhibit platelet aggregation. The compounds are substantially free of beta-adrenergic blocking effects which inhibit peripheral vasodilating activity of beta-adrenergic stimulatory endogenous amines. Standard in vivo and in vitro pharmacological test methods can be employed in assessing the activity of compounds characterized by formula I. For instance, the perfused dog hind limb preparation is considered particularly useful in measuring vasodilator activity. The preferred compounds N-[3-[4-(methylthio)phenoxy]propyl]octylamine hydrochloride and N-[3-[4-[(1-methylethyl)thio]phenoxy]propyl]octylamine hydrochloride, which produce a 50 mm Hg fall in perfusion pressure at infusion doses of 0.7 and 0.32 mg./min., respectively, are representative of the activity of the compounds of the instant invention in this test. Papaverine, a well-known vasodilating agent, reduces pressure by a 50 mm Hg at an infusion dose of 0.76 mg./min. Antispasmodic activity is determined by spasmogen-challenged rabbit aortic strip with antithrombogenic action demonstrated by inhibition of adenosine diphosphate and collagen-induced platelet aggregation in human platelet-rich plasma. The isoproterenol challenged guinea pig trachea test, which is standard in the art, is suitable for measuring beta-adrenergic blocking action.

Another aspect of the instant invention concerns a therapeutic process for treating a mammal requiring vasodilation which comprises systemically administering to the mammal an effective vasodilating amount of a compound selected from the group characterized by formula I and pharmaceutically acceptable non-toxic acid addition salt thereof.

As used herein, the term "effective vasodilating amount" is construed to mean a dose which exerts a vasodilator effect in the effected mammal without untoward side effects.

By systemic administration, it is intended to include both oral and parenteral routes. Examples of parenteral administration are intramuscular, intravenous, intraperitoneal, rectal, and subcutaneous administration. In rectal administration, both ointments and suppositories may be employed. While the dosage will vary to some extent with the mode of administration and the particular compound chosen, from about 0.5 mg. per kg. body weight to 25 mg. per kg. body weight of a compound characterized by formula I or non-toxic pharmaceutically acceptable salts thereof administered in effective single or multiple dosage units generally provides the desired vasodilating effect.

In carrying out the therapeutic process of the instant invention, the formula I compounds are generally administered for vasodilating purposes in the form of a pharmaceutical preparation containing either a formula I free base or a pharmaceutically acceptable non-toxic acid addition salt thereof as the active component in combination with a pharmaceutically acceptable carrier. The carrier may be solid, semi-solid, liquid diluent or a capsule. Accordingly, a further feature of the instant invention is directed to pharmaceutical compositions containing the compounds of formula I or non-toxic pharmaceutically acceptable acid addition salts thereof in combination with a pharmaceutically acceptable carrier.

For the preparation of pharmaceutical compositions containing the compounds of formula I in the form of dosage units for oral administration, the compound is mixed with a solid, pulverulent carrier, (e.g., lactose, sucrose, sorbitol, mannitol, potato starch, corn starch, amylopectin, cellulose derivatives, or gelatin) as well as with an anti-friction agent (e.g., magnesium stearate, calcium stearate, polyethylene glycol waxes or the like) and pressed into tablets. The tablets may be used uncoated or coated by conventional techniques to delay disintegration and absorption in the gastrointestinal tract thereby providing a sustained action over a longer time period. If coated tablets are wanted, the above prepared core may be coated with concentrated solution of sugar, which solution may contain, e.g., gum, arabic, gelatin, talc, titanium dioxide, or the like. Furthermore, tablets may be coated with a lacquer dissolved in an easily volatile organic solvent or mixture of solvents. If desired, dye may be added to this coating.

In the preparation of soft gelatin capsules or in the preparation of similar closed capsules, the active compound is mixed with a vegetable oil. Hard gelatin capsules may contain granules of the active ingredient in combination with a solid, pulverulent carrier such as lactose, saccharose, sorbitol, starch, (e.g., potato starch, corn starch, or amylopectin), cellulose derivatives or gelatin.

Dose units for rectal administration may be prepared in the form of suppositories containing the active substance of formula I in mixture with a neutral fat base, or they may be prepared in form of gelatin-rectal capsules containing the active substance in a mixture with a vegetable oil or paraffin oil.

Liquid preparations for oral administration may be present in the form of elixirs, syrups or suspensions containing from about 0.2% by weight to about 20% by weight of the active ingredient. Such liquid preparations may contain coloring agents, flavoring agents, sweetening agents, and carboxymethylcellulose as a thickening agent.

Suitable solutions for parenteral administration by injection may be prepared as an aqueous solution of a water-soluble pharmaceutically acceptable salt of the compounds of formula I adjusted to a physiologically acceptable pH. These solutions may also contain stabilizing agents.

Pharmaceutical tablets for oral use are prepared by conventional methods involving mixing the therapeutic compound of formula I and necessary axillary agents.

The following examples are given solely for the purpose of illustration and are not to be construed as limitations of this invention, many variations of which are possible without departing from the spirit or scope thereof.

EXAMPLE 1

N-[3-[4-(Methylthio)phenoxy]propyl]octylamine Hydrochloride

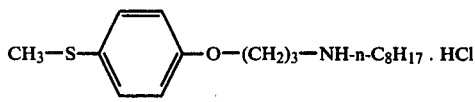

(a) A solution of 4-(methylthio)phenol (10.0 g, 0.071 mole) in 150 ml. of 1,2-dimethoxyethane is added to a slurry of a 57% dispersion of sodium hydride (3.0 g., 0.071 mole) in mineral oil (previously washed with hexane to remove the mineral oil) in 100 ml. of 1,2-dimethoxyethane. After the initial reaction is complete, 1-bromo-3-chloropropane (12.63 g., 0.08 mole) is added in one portion. The resulting mixture is stirred and refluxed for a period of 68 hrs., cooled and then concentrated under reduced pressure. Residual material (oil) is dissolved in ether and washed with water. The ether solution (after drying over magnesium sulfate) is concentrated under reduced pressure to provide 14.6 g. of an oil containing approximately 25% starting phenol according to NMR spectra. Distillation of the oil under reduced pressure affords, after a forerun of 4-(methylmercapto)phenol, 5.0 g. (32% yield) of 1-chloro-3-[4-(methylthio)phenoxy]propane, b.p. 150°-152° C. at 27 mm Hg.

(b) A solution of 1-chloro-3-[4-(methylthio)phenoxy]propane (5.0 g., 0.023 mole) in 30 ml. of ethanol is treated with n-octylamine (2.84 g., 0.022 mole) and 30 mg. of potassium iodide. After refluxing for a period of 18 hrs., the reaction mixture is concentrated to dryness under reduced pressure, treated with 3N potassium hydroxide solution and ether, and the layers separated. The ether layer is washed with water, concentrated under reduced pressure, and heated on a steam bath at 0.1 mm Hg pressure to remove residual n-octylamine. The residue of N-[3-[4-(methylthio)phenoxy]propyl]octylamine base thus obtained is dissolved in ethanol, treated with excess 6N hydrochloric acid and activated charcoal, filtered and concentrated to dryness under reduced pressure. Crystallization of the residue from isopropyl alcohol-ether affords 1.7 g. (22% yield) of analytically pure N-[3-[4-(methylthio)phenoxy]propyl]octylamine hydrochloride, m.p. 214.5°-215.5° C. (corr.).

Anal. Calcd. for $C_{18}H_{31}NOS \cdot HCl$: C, 62.49; H, 9.32; N, 4.05. Found: C, 62.44; H, 9.36; N, 3.90.

EXAMPLE 2

N-[3-[4-[(1-Methylethyl)thio]phenoxy]propyl]octylamine Hydrochloride

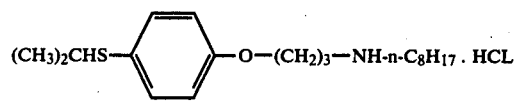

(a) A solution of 4-(1-methylethylthio)phenol (16.83 g., 0.1 mole) in 150 ml. of isopropyl alcohol is treated with 5.2 ml. of 50% sodium hydroxide solution (0.10 mole) and 2 ml. of water. To this mixture is added in one portion 1-bromo-3-chloropropane (16.5 g., 0.105 mole) and the mixture stirred and refluxed for a period of 20 hrs. After cooling, the reaction mixture is concentrated under reduced pressure and the resulting residue extracted with ether. The ethereal extract is filtered, concentrated under reduced pressure and the oily residue distilled affording 4.8 g. (20% yield) of 1-chloro-3-[4-(1-methylethylthio)phenoxy]propane, b.p. 136°-140° C. at 0.6 mm Hg.

(b) A mixture of 1-chloro-3-[4-(1-methylethylthio)phenoxy]propane (4.8 g., 0.02 mole), n-octylamine (2.53 g., 0.02 mole), potassium carbonate (5.42 g., 0.039 mole) in 150 ml. of acetonitrile is stirred and refluxed for a 23 hr. period. The cooled reaction mixture is filtered and the filtrate concentrated under reduced pressure to provide an oil. The oily residue is dissolved in ether, filtered and concentrated again to an oil. Unreacted n-octylamine is removed by distillation (heating the oil 80° C. at 0.1 mm Hg). Residual material is dissolved in ether and treated with excess ethanolic hydrogen chloride to provide the insoluble hydrochloride salt. Crystallization of the salt from isopropyl alcohol-ether affords 1.63 g. (22% yield) of N-[3-[4-[(1-methylethyl)thio]phenoxy]propyl]octylamine hydrochloride, m.p. 193.5°-195.5° C. (corr.).

Anal. Calcd. for $C_{20}H_{35}NOS \cdot HCl$: C, 64.23; H, 9.70; N, 3.74. Found: C, 64.34; H, 9.70; N, 3.58.

EXAMPLE 3

N-[3-[4-[(1-Methylethyl)thio]phenoxy]propyl]-2,2-dimethylhex-1-ylamine

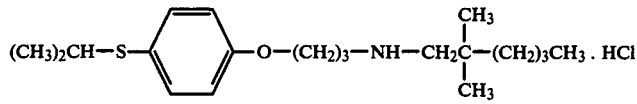

(a) 2,2-Dimethylhex-1-ylamine—A solution of capronitrile (25 g., 0.26 mole) and methyl iodide (75 g., 0.53 Mole) in 80 ml. of dry toluene is warmed to 80° and treated gradually with a suspension of sodium amide (25.4 g., 0.65 mole) in 100 ml. of toluene at a rate sufficient to maintain general reflux. After addition is complete, the mixture is stirred and refluxed for an additional 2 hr. period, cooled and treated with 150 ml. of water. The organic layer is separated, washed with water and dried over magnesium sulfate. Concentration of the dried solution under reduced pressure and distillation of residual material affords an 81% yield of 2,2-dimethylcapronitrile.

A solution of 2,2-dimethylcapronitrile (10.0 g., 0.078 mole) in 100 ml. of ether is added slowly to a suspension of lithium aluminum hydride (6.0 g., 0.158 mole) in 200 ml. of ether while maintaining the reaction at 0°–5°. After stirring the reaction mixture for an additional 2 hr., at 0.5°, the mixture is hydrolyzed by sequentially adding 6.0 ml. of water, 6.0 ml. of 15% sodium hydroxide solution, and finally 18 ml. of water. The hydrolyzed mixture is stirred for an additional hour, filtered and the ether phase concentrated under reduced pressure. Distillation of residual material provides 2,2-dimethylhex-1-ylamine.

(b) Reaction of 1-chloro-3-[4-(1-methylethylthio)-phenoxy]propane with 2,2-dimethylhex-1-ylamine according to the procedure of Example 2(b) and conversion of the base to the hydrochloride provides N-[3-[4-[(1-methylethyl)thio]phenoxy]propyl]-2,2-dimethylhex-1-ylamine hydrochloride.

EXAMPLE 4

N-[3-[4-[(1-Methylethyl)thio]phenoxy]propyl]-2-methyl-2-octylamine Hydrochloride

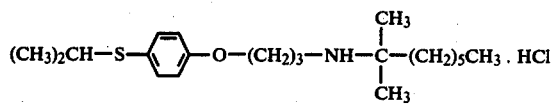

(a) 2-Methyl-2-octanol—A solution of methylheptanoate (14.5 g., 0.1 mole) in 200 ml. of ether is added to 200 ml. of 3M solution (0.6 mole) of methyl magnesium bromide in ether at a rate sufficient to maintain refluxing. After addition is complete, the resulting mixture is refluxed for 1 hr. and then stirred at 26° for a 16 hour period. The mixture is hydrolyzed by the addition of dilute ammonium chloride solution, filtered and the filter cake dissolved in 2N hydrochloric acid and extracted with ether. The ethereal extract and filtrate are combined, sequentially washed with water, dilute sodium bicarbonate solution and brine and dried over magnesium sulfate. Concentration of the dried solution and distillation of residual material under reduced pressure provides 13.1 g. (91% yield) of 2-methyl-2-octanol, b.p. 130° (100 mm Hg).

(b) N-(2-Methyl-2-octyl)acetamide—A solution of concentrated sulfuric acid (5.55 g., 0.055 mole) in 32 ml. of glacial acetic acid is treated with acetonitrile (2.5 g., 0.016 mole) and 2-methyl-2-octanol (8.0 g., 0.055 mole) and the resulting mixture stirred at 26° for a 17 hr. period. After diluting with 125 ml. of water, the mixture is extracted with ether and the ethereal extract sequentially washed with water, dilute sodium bicarbonate solution and brine and dried over magnesium sulfate. Concentration of the dried solution provides 8.7 g. (85% yield) of N-(2-methyl-2-octyl)acetamide which is used in the next step without further purification.

(c) 2-Methyl-2-octylamine—A solution of potassium hydroxide (10.0 g., 0.18 mole) in 100 ml. of ethylene glycol is treated with N-(2-methyl-2-octyl)acetamide (13.0 g., 0.07 mole) and the mixture heated at 200° for a 64 hr. period. The reaction mixture is diluted with 400 ml. of water and extracted with ether. The ethereal extract is washed with water and brine and then dried over sodium sulfate. Concentration of the dried solution under reduced pressure affords 10.4 g. (62% yield) of 2-methyl-2-octylamine which is used in the next step without further purification.

(d) N-[3-[4-[(1-Methylethyl)thio]phenoxy]propyl]-2-methyl-2-octylamine Hydrochloride Preparation—Reaction of 1-chloro-3-[4-(1-methylethylthio)-phenoxy]propane with 2-methyl-2-octylamine according to the procedure of Example 2(b) and conversion of the base to the hydrochloride provides N-[3-[4-[(1-methylethyl)thio]phenoxy]propyl]-2-methyl-2-octylamine hydrochloride.

EXAMPLE 5

N-[2-[4-[(1-Methylethyl)thio]phenoxy]ethyl]octylamine Hydrochloride

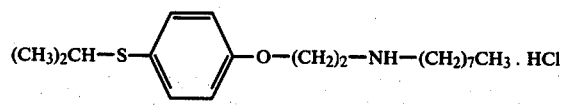

According to the procedure of Example 1, 1-chloro-2-[4-(methylthio)phenoxy]ethane from 4-(methylthio)-phenol and 1-chloro-2-bromoethane is reacted with n-octylamine to provide N-[2-[4-[(1-methylethyl)thio]-phenoxy]ethyl]octylamine hydrochloride.

EXAMPLE 6

The following compounds of Table A are prepared according to the procedures of Examples 1 and 2 by reacting the alkylthiophenoxypropyl chloride intermediate obtained from the starting phenol and 1-bromo-3-chloropropane with n-octylamine.

TABLE A

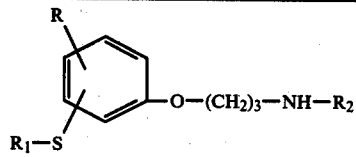

| Ex. | Starting Thiophenol | Product R | $R_1S$ |
|---|---|---|---|
| 6 | 4-ethylthiophenol | H | 4-$C_2H_5S$ |
| 7 | 4-n-propylthiophenol | H | 4-n-$C_3H_7S$ |
| 8 | 4-n-butylthiophenol | H | 4-n-$C_4H_9S$ |
| 9 | 4-n-pentylthiophenol | H | 4-n-$C_5H_{11}S$ |
| 10 | 4-n-hexylthiophenol | H | 4-n-$C_6H_{13}S$ |
| 11 | 4-n-heptylthiophenol | H | 4-n-$C_7H_{15}S$ |
| 12 | 4-n-octylthiophenol | H | 4-n-$C_8H_{17}S$ |
| 13 | 4-(3-methylbutylthio)phenol | H | 4-$(CH_3)_2CHCH_2CH_2S$ |
| 14 | 2-n-butylthiophenol | H | 2-n-$C_4H_9S$ |
| 15 | 3-n-butylthiophenol | H | 3-n-$C_4H_9S$ |
| 16 | 2-ethylthiophenol | H | 2-$C_2H_5S$ |
| 17 | 2-n-propylthiophenol | H | 2-n-$C_3H_7S$ |
| 18 | 2-isopropylthiophenol | H | 2-i-$C_3H_7S$ |
| 19 | 3-ethylthiophenol | H | 3-$C_2H_5S$ |
| 20 | 3-n-propylthiophenol | H | 3-n-$C_3H_7S$ |
| 21 | 3-isopropylthiophenol | H | 3-i-$C_3H_7S$ |
| 22 | 2-methyl-4-(methylthio)phenol | 2-$CH_3$ | 4-$CH_3S$ |
| 23 | 3-methyl-4-(methylthio)phenol | 3-$CH_3$ | 4-$CH_3S$ |

EXAMPLE 24

Tablets

The following ingredients are blended into proportion by weight indicated according to conventional pharmaceutical techniques to provide a tablet base.

| Ingredient | Amount |
| --- | --- |
| Lactose | 79 |
| Corn starch | 10 |
| Talcum | 6 |
| Tragancanth | 4 |
| Magnesium stearate | 1 |

This tablet base is blended with sufficient N-[3-[4-[(1-methylethyl)thio]phenoxy]propyl]octylamine hydrochloride to provide tablets containing 10, 20, 40, 80, 160 and 320 mg. of active ingredient and compressed into conventional tablet press.

EXAMPLE 25

Dry-Filled Capsules

The following ingredients are blended in a conventional manner in the proportion by weight indicated.

| Ingredient | Amount |
| --- | --- |
| Lactose, U.S.P. | 50 |
| Starch | 5 |
| Magnesium stearate | 2 |

Sufficient N-[3-[4-[(1-methylethyl)thio]phenoxy]propyl-octylamine hydrochloride is added to the blend to provide capsules containing 10, 20, 40, 80, 160 and 320 mg. of active ingredient which is filled into hard gelatin capsules of a suitable size.

What is claimed is:

1. A compound of the formula

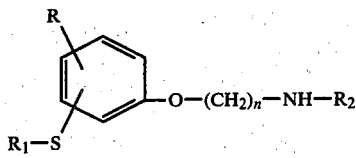

wherein
R is hydrogen or lower alkyl of 1 to 4 carbon atoms inclusive;
$R_1$ is alkyl of 1 to 8 carbon atoms inclusive;
$R_2$ is alkyl of 6 to 12 carbon atoms inclusive;
n is the integer 2 or 3;
or the pharmaceutically acceptable acid addition salts thereof.

2. The compound according to claim 1 which is N-[3-[4-(methylthio)phenoxy]propyl]octylamine or a non-toxic pharmaceutically acceptable salt thereof.

3. The compound of claim 1 which is N-[3-[4-(methylthio)phenoxy]propyl]octylamine hydrochloride.

4. The compound according to claim 1 which is N-[3-[4-[(1-methylethyl)thio]phenoxy]propyl]octylamine or a non-toxic pharmaceutically acceptable salt thereof.

5. The compound of claim 1 which of N-[3-[4-[(1-methylethyl)thio]phenoxy]propyl]octylamine hydrochloride.

6. The compound according to claim 1 wherein R is hydrogen, $R_1$ is ($C_1$–$C_8$) alkyl, $R_2$ is ($C_6$–$C_{12}$) alkyl, and n is 2 or 3.

7. The compound according to claim 1 wherein R is hydrogen, $R_1$ is ($C_1$–$C_8$) alkyl, $R_2$ is ($C_6$–$C_{12}$) alkyl, and n is 3.

8. The compound according to claim 1 wherein R is hydrogen, $R_1$ is lower ($C_1$–$C_4$) alkyl with the $R_1S$ radical in the para position, $R_2$ is ($C_6$–$C_{12}$) alkyl, and n is 2 or 3.

9. The compound according to claim 1 wherein R is hydrogen, $R_1$ is lower ($C_1$–$C_4$) alkyl with the $R_1S$ radical in the para position, and $R_2$ is ($C_6$–$C_{12}$) alkyl, and n is 3.

10. The compound according to claim 1 wherein R is hydrogen, $R_1$ is lower ($C_1$–$C_4$) alkyl with the $R_1S$ radical in the para position, $R_2$ is n-octyl, and n is 2 or 3.

11. The compound according to claim 1 wherein R is hydrogen, $R_1$ is lower ($C_1$–$C_4$) alkyl with the $R_1S$ radical in the para position, $R_2$ is n-octyl, and n is 3.

12. The compound according to claim 1 wherein R is hydrogen, $R_1$ is isopropyl, $R_2$ is ($C_6$–$C_{12}$) alkyl and n is 2.

13. The compound according to claim 1 wherein R is hydrogen, $R_1$ is isopropyl, $R_2$ is ($C_6$–$C_{12}$) alkyl and n is 3.

14. The compound according to claim 1 wherein R is hydrogen, $R_1$ is isopropyl with the $R_1S$ radical in the para position, $R_2$ is ($C_6$–$C_{12}$) alkyl and n is 3.

15. The compound according to claim 1 wherein R is hydrogen, $R_1$ is isopropyl with the $R_1S$ radical in the para position, $R_2$ is n-octyl, and n is 2 or 3.

16. The compound according to claim 1 wherein R is methyl, $R_1$ is lower ($C_1$–$C_4$) alkyl with the $R_1S$ radical in the para position, $R_2$ is n-octyl, and n is 3.

17. The therapeutic process of treating vascular disease which comprises administering to a mammal requiring vasodilation an effective vasodilating amount of a compound of the formula

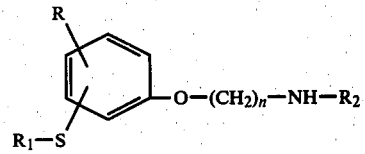

wherein
R is hydrogen or lower alkyl of 1 to 4 carbon atoms inclusive;
$R_1$ is alkyl of 1 to 8 carbon atoms inclusive;
$R_2$ is alkyl of 6 to 12 carbon atoms inclusive;
n is the integer 2 or 3;
or the pharmaceutically acceptable acid addition salts thereof.

18. The process of claim 17 wherein said compound is N-[3-[4-(methylthio)phenoxy]propyl]octylamine or a non-toxic pharmaceutically acceptable salt thereof.

19. The process of claim 17 wherein said compound is N-[3-[4-(methylthio)phenoxy]propyl]octylamine hydrochloride.

20. The process of claim 17 wherein said compound is N-[3-[4-[(1-methylethyl)thio]phenoxy]propyl]octylamine or a non-toxic pharmaceutically acceptable salt thereof.

21. The process of claim 17 wherein said compound is N-[3-[4-[(1-methylethyl)thio]phenoxy]propyl]octylamine hydrochloride.

* * * * *